US 6,678,554 B1

(12) United States Patent
Sun et al.

(10) Patent No.: US 6,678,554 B1
(45) Date of Patent: Jan. 13, 2004

(54) ELECTROTRANSPORT DELIVERY SYSTEM COMPRISING INTERNAL SENSORS

(75) Inventors: Ying Sun, Somerville, NJ (US); Ralph W. Oakeson, Racine, WI (US); Stephen J. Wisniewski, Doylestown, PA (US); Jonas C. T. Wang, West Windsor, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 09/549,147

(22) Filed: Apr. 13, 2000

Related U.S. Application Data
(60) Provisional application No. 60/129,807, filed on Apr. 16, 1999.

(51) Int. Cl.[7] .................................................. A61N 1/32
(52) U.S. Cl. ........................................................ 604/20
(58) Field of Search ........................... 604/20, 21, 93.01, 604/288.01, 288.02, 288.03, 288.04

(56) References Cited

U.S. PATENT DOCUMENTS

| 2,857,356 A | 10/1958 | Goodwin |
| 3,315,665 A | 4/1967 | MacLeon |
| 3,950,158 A | 4/1976 | Gossett |
| 3,964,482 A | 6/1976 | Gerstel et al. |
| 4,039,707 A | 8/1977 | O'Malley |
| 4,071,028 A | 1/1978 | Perkins |
| 4,141,359 A | 2/1979 | Jacobsen et al. |
| 4,230,105 A | 10/1980 | Harwood |
| 4,231,372 A | 11/1980 | Newton |
| 4,301,794 A | 11/1981 | Tapper |
| 4,340,047 A | 7/1982 | Tapper et al. |
| 4,406,658 A | 9/1983 | Lattin et al. ................ 604/20 |
| 4,532,924 A | 8/1985 | Auth et al. |
| 4,655,766 A | 4/1987 | Theeuwes et al. |
| 4,655,767 A | 4/1987 | Woodard et al. |
| 4,674,499 A | 6/1987 | Pao |

(List continued on next page.)

FOREIGN PATENT DOCUMENTS

| DE | 195 25 607 A1 | 7/1995 |
| EP | 0 429 842 A2 | 10/1990 |

(List continued on next page.)

OTHER PUBLICATIONS

PCT International Search Report dated Dec. 06, 1999.
PCT International Search Report dated Aug. 21, 2000.
PCT International Search Report dated Aug. 11, 2000.

(List continued on next page.)

Primary Examiner—Edward K. Look
Assistant Examiner—Richard A. Edgar
(74) Attorney, Agent, or Firm—William E. McGowan

(57) ABSTRACT

The present invention relates to an apparatus for the delivery of an active agent through a body surface of a mammal comprising: (a) a housing with a delivery orifice through the housing; (b) a reservoir within the housing for containing the active where the reservoir is in communication with the delivery orifice; (c) an electrode within the reservoir where the electrode is capable of being in electronic communication with a current supply unit; and (d) a sensor within the reservoir where the sensor is capable of being in electronic communication with the current supply unit; wherein the current supply unit can modify an electric parameter at the electrode based upon feedback from the sensor.

22 Claims, 7 Drawing Sheets

U.S. PATENT DOCUMENTS

| | | |
|---|---|---|
| 4,685,911 A | 8/1987 | Konno et al. |
| 4,722,726 A | 2/1988 | Sanderson et al. |
| 4,731,049 A | 3/1988 | Parsi |
| 4,744,788 A | 5/1988 | Mercer, Jr. |
| 4,747,819 A | 5/1988 | Phipps et al. |
| 4,752,285 A | 6/1988 | Petelenz et al. |
| 4,767,402 A | 8/1988 | Kost et al. |
| 4,790,824 A | 12/1988 | Morrow et al. |
| 4,805,616 A | 2/1989 | Pao |
| 4,898,920 A | 2/1990 | Lee et al. |
| 4,925,671 A | 5/1990 | Abber et al. |
| 4,927,408 A | 5/1990 | Haak et al. |
| 4,963,360 A | 10/1990 | Argaud |
| 4,979,948 A | 12/1990 | Geddes et al. |
| 4,994,267 A | 2/1991 | Sablotsky |
| 5,013,293 A | 5/1991 | Sibalis |
| 5,019,034 A | 5/1991 | Weaver et al. |
| 5,036,861 A | 8/1991 | Sembrowich et al. |
| 5,042,975 A | 8/1991 | Chien et al. |
| 5,098,430 A | 3/1992 | Fleenor |
| 5,125,928 A | 6/1992 | Parins et al. |
| 5,135,478 A | 8/1992 | Sibalis |
| 5,147,916 A | 9/1992 | Sweet |
| 5,156,591 A | 10/1992 | Gross et al. |
| 5,162,410 A | 11/1992 | Sweet |
| 5,182,938 A | 2/1993 | Merkel |
| 5,213,568 A | 5/1993 | Lattin et al. |
| 5,224,927 A | 7/1993 | Tapper |
| 5,232,702 A | 8/1993 | Pfister et al. |
| 5,250,023 A | 10/1993 | Lee et al. |
| 5,252,334 A | 10/1993 | Chiang et al. |
| 5,269,780 A | 12/1993 | Roos |
| 5,279,543 A | 1/1994 | Glikfeld et al. |
| 5,279,544 A | 1/1994 | Gross et al. |
| 5,282,799 A | 2/1994 | Rydell |
| 5,304,468 A | 4/1994 | Phillips et al. |
| 5,320,607 A | 6/1994 | Ishibashi |
| 5,362,307 A | 11/1994 | Guy et al. |
| 5,383,917 A | 1/1995 | Desai et al. |
| 5,386,837 A | 2/1995 | Sterzer |
| 5,399,163 A | 3/1995 | Peterson et al. |
| 5,438,984 A | 8/1995 | Schoendorfer |
| 5,441,490 A | 8/1995 | Svedman |
| 5,451,224 A | 9/1995 | Goble et al. |
| 5,453,360 A | 9/1995 | Yu |
| 5,514,130 A | 5/1996 | Baker |
| 5,527,288 A | 6/1996 | Gross et al. |
| 5,533,971 A | 7/1996 | Phipps |
| 5,540,669 A | 7/1996 | Sage, Jr. et al. |
| 5,540,681 A | 7/1996 | Strul et al. |
| 5,542,916 A | 8/1996 | Hirsch et al. |
| 5,545,161 A | 8/1996 | Imran |
| 5,547,467 A | 8/1996 | Pliquett et al. |
| 5,563,031 A | 10/1996 | Yu |
| 5,563,042 A | 10/1996 | Phillips et al. |
| 5,571,149 A | 11/1996 | Liss et al. |
| 5,573,778 A | 11/1996 | Therriault et al. |
| 5,582,586 A | 12/1996 | Tachibana et al. |
| 5,591,124 A | 1/1997 | Phipps ..................... 604/20 |
| 5,614,502 A | 3/1997 | Flotte et al. |
| 5,622,530 A | 4/1997 | Phipps |
| 5,636,632 A | 6/1997 | Bommannan et al. |
| 5,647,844 A * | 7/1997 | Haak et al. ............... 604/20 X |
| 5,658,583 A | 8/1997 | Zhang et al. |
| 5,658,892 A | 8/1997 | Flotte et al. |
| 5,662,624 A | 9/1997 | Sundstrom et al. |
| 5,667,491 A | 9/1997 | Pliquett et al. |
| 5,693,052 A | 12/1997 | Weaver |
| 5,718,955 A | 2/1998 | McGuire et al. |
| 5,735,273 A | 4/1998 | Limol et al. |
| 5,738,107 A | 4/1998 | Martinsen et al. |
| 5,749,847 A | 5/1998 | Zewert et al. |
| 5,771,890 A | 6/1998 | Tamada |
| 5,780,050 A | 7/1998 | Jain et al. |
| 5,785,705 A | 7/1998 | Baker |
| 5,789,255 A | 8/1998 | Yu |
| 5,827,183 A | 10/1998 | Kurnick et al. |
| 5,843,114 A | 12/1998 | Jang |
| 5,843,692 A | 12/1998 | Phillips et al. |
| 5,853,383 A | 12/1998 | Murdock |
| 5,857,992 A | 1/1999 | Haak et al. |
| 5,865,788 A | 2/1999 | Edwards et al. |
| 5,869,326 A | 2/1999 | Hofmann |
| 5,893,885 A | 4/1999 | Webster, Jr. |
| 5,897,553 A | 4/1999 | Mulier et al. |
| 5,906,613 A | 5/1999 | Mulier et al. |
| 5,993,434 A | 11/1999 | Dev et al. |
| 6,014,584 A | 1/2000 | Hofmann et al. |
| 6,050,988 A | 4/2000 | Zuck |
| 6,055,043 A | 4/2000 | Chambers |
| 6,068,650 A | 5/2000 | Hofmann et al. |
| 6,083,196 A | 7/2000 | Trautman et al. |
| 6,096,020 A | 8/2000 | Hofmann |
| 6,104,952 A | 8/2000 | Tu et al. |
| 6,117,660 A | 9/2000 | Walters et al. |
| 6,120,493 A | 9/2000 | Hofmann |
| 6,148,232 A | 11/2000 | Arrahami |
| 6,181,964 B1 | 1/2001 | Hofmann et al. |
| 6,597,947 B1 * | 7/2003 | Inoue et al. .................. 604/20 |

FOREIGN PATENT DOCUMENTS

| | | |
|---|---|---|
| GB | 2 303 208 A | 2/1997 |
| WO | WO 86/07269 | 12/1986 |
| WO | WO 92/07618 | 5/1992 |
| WO | WO 93/17754 | 9/1993 |
| WO | WO 94/23777 | 10/1994 |
| WO | WO 95/30410 | 11/1995 |
| WO | WO 96/00110 | 1/1996 |
| WO | WO 96/17648 | 6/1996 |
| WO | WO 96/37256 | 11/1996 |
| WO | 97/04832 A1 | 2/1997 |
| WO | WO 97/12644 | 4/1997 |
| WO | WO 97/48440 | 12/1997 |
| WO | WO 97/48441 | 12/1997 |
| WO | WO 97/48442 | 12/1997 |
| WO | WO 98/11937 | 3/1998 |
| WO | WO 98/28037 | 7/1998 |
| WO | WO 98/28038 | 7/1998 |
| WO | 98/29134 A2 | 7/1998 |
| WO | WO 98/46124 | 10/1998 |
| WO | WO 99/22809 A1 | 5/1999 |

OTHER PUBLICATIONS

Sun, Y. (1997) Skin Absorption Enhancement by Physical Means: Heat, Ultrasound, and Electricity. Transdermal and Topical Drug Delivery Systems.327–355.

Buyuktimkin N., Buyuktimkin S. (1997) Chemcial Means of Transdermal Drug Permeation Enhancement. Transdermal and Topical Drug Delivery Systems. 357–475.

Sun Y., Liu J.C., Xue H. (1990) Important Parameters Affecting Iontophoretic Transdermal Delivery of Insulin. Proceed. Intern. Symp. Control. Rel. Bioact. Mater., 17, Controlled Release Society, Inc. 202–203.

Roberts M. Lai P., Cross S., Yoshida N. (1997) Solute Structure as a Determinant of Iontophoretic Transport. Mechanisms of Transdermal Drug Delivery. 291–349.

PCT Search Report dated Nov. 8, 2000 of International application No. PCT/US 00/ 09955.

U.S. patent application Ser. No. 09/548,771, Pending, Johnson & Johnson Consumer Companies, Inc.

U.S. patent applicaion Ser. No. 09/385,284, Pending, Johnson & Johnson Consumer Companies, Inc.

U.S. patent application Ser. No. 09/644,093, Pending, Johnson & Johnson Consumer Companies, Inc.

U.S. patent application Ser. No. 09/611,865, Pending, Johnson & Johnson Consumer Companies, Inc.

U.S. patent application Ser. No. 09/612,357, Pending, Johnson & Johnson Consumer Companies, Inc.

U.S. patent application Ser. No. 09/795,908, Pending, Johnson & Johnson Consumer Companies, Inc.

Pending application "Tissue Ablation by Shear Force for Sampling Biological Fluids and Delivering Active Agents" filed Apr. 30, 2001Johnson & Johnson Consumer Companies Inc.

Sun, "Skin Absorption Enhancement By Physical Means: Heat, Ultrasound, and Electricity", *Transdermal and Topical Drug Delivery Systems*, Gosh, et al. Ed. Interpharm Press, Inc. 1997, pp. 327–355.

Roberts, et all., "Solute Structure as a Determinant of Iontophoretic Transport", *Mechanisms of Transdermal Drug Delivery*, Potts, et al. Ed. Marcel Dekker, 1997, pp. 291–349.

Sun, et al., "Important Parameters Affecting Iontophoretic Transdermal Delivery of Insuln", *Proceed. Intern. Symp. Control.Rel. Bioact. Mater.*, 17 (1990), Controlled Release Society, Inc., 17: 202–203.

Henry, et al., "Microfabricated Microneedles: A Novel Approach to Transdermal Drug Delivery", *J. Pharm. Sci.* vol. 87, No. 8, Aug. 1998, pp. 922–925.

Cosofret, et al., "Pharmaceutical Applications of Membrane Sensors", *Boca Raton, FL: CRC Press*, 1992.

Park, "Constant Current Source for Iontophoresis", *Journal of Neuroscience Methods*, 29 (1989), pp. 85–89.

Zakzewski, et al., "Design and Implementation of a Constant–Current Pulsed Iontophoretic Stimulation Device", *Med. & Biol. Eng. & Comput.*, 1996, 34, pp. 484–488.

Jaw, et al., "Portable Current Stimulator For Transdermal Iontophoretic Drug Delivery", *med. Eng. Phys. 1995*, vol. 17, pp. 385–386, Jul.

* cited by examiner

US 6,678,554 B1

ELECTROTRANSPORT DELIVERY SYSTEM COMPRISING INTERNAL SENSORS

RELATED APPLICATIONS

This application is a continuation-in-part of application Ser. No. 60/129,807 filed Apr. 16, 1999, which his incorporated herein by reference.

FIELD OF THE INVENTION

The present invention relates to an electricity-assisted delivery system for transporting active agents across a body surface of a mammal (e.g., the skin or mucosa of a human). This system delivers active agents more efficiently than prior electrotransport systems.

BACKGROUND OF THE INVENTION

Transdermal and topical dosage forms have been widely prescribed for decades in the treatment of systemic diseases and local conditions such as those involved with the skin and underlying tissues. Electricity may be employed to facilitate drug transport across the skin barrier. In electricity-assisted transdermal drug delivery, an electric potential (voltage) is applied to the skin to facilitate drug transport. There are three primary types of electricity-assisted drug transport through the skin barrier: iontophoresis, electro-osmosis and electroporation. In transdermal iontophoresis, an ionized drug migrates into the skin driven by an applied electric potential gradient. In electro-osmosis, a non-ionic drug to be delivered is carried by a fluid, which is driven across the skin by an applied electric potential gradient. Electroporation is the microscopic perforation of the skin barrier by extremely short pulses of high electric voltage and low electric current. These methods are described in a recent review by Sun, "Skin Absorption Enhancement by Physical Means: Heat, Ultrasound, and Electricity", *Transdermal and Topical Drug Delivery Systems,* Ghosh, et al. Ed. Interpharm Press, Inc., 1997, pages 327–355, and Roberts, et al., "Solute Structure as a Determinant of Iontophoretic Transport", *Mechanisms of Transdermal Drug Delivery,* Potts, et al. Ed. Marcel Dekker, 1997, pages 291–349.

In practice, there is often more than one type of the electricity-assisted drug delivery methods being employed with one drug delivery system. For example, an electrotransport system may actually deliver the active agent simultaneously with both iontophoresis and electro-osmosis. Similarly, electroporation can be used first to increase the skin permeability, followed by iontophoresis to transport the active agent through the skin barrier. In most of the cases there are little differences among the three types of electricity-assisted delivery methods in the construction of the apparatus (e.g., the drug reservoir, conductive electrode, and a counter electrode), except for the electric current supply unit.

SUMMARY OF THE INVENTION

In one aspect, the present invention relates to an apparatus for the delivery of an active agent through a body surface of a mammal (e.g., a human) comprising: (a) a housing with a delivery orifice through the housing; (b) a reservoir within the housing for containing the active agent (e.g., an ionic drug) within a fluid (e.g., a low electrolyte aqueous solution such as distilled water) where the reservoir is in communication with the delivery orifice; (c) an electrode within the reservoir where the electrode is capable of being in electronic communication with a current supply unit; and (d) a sensor within the reservoir where the sensor is capable of being in electronic communication with the current supply unit; wherein the current supply unit can modify an electric parameter at the electrode based upon feedback from the sensor. In one embodiment, the electric parameter is selected from the group consisting of current intensity, current mode, current waveform, voltage, and polarity.

The sensor measures compositional or electrical changes in the reservoir. Examples of such sensors include sensors that measure pH, conductivity, impedance, the active agent, ions, and biological compounds. In another embodiment, the apparatus comprises more than one sensor within the reservoir.

In another embodiment, the reservoir comprises: an active agent reservoir within the housing for containing the active agent where the active agent reservoir is in communication with the delivery orifice; a fluid reservoir within the housing for containing a fluid; and a semi-permeable membrane in communication with the active agent reservoir and the fluid reservoir. The semi-permeable membrane is capable of both permitting the movement of fluid (e.g., water and non-active agents solubilized therein) between the active agent reservoir and the fluid reservoir and substantially preventing the movement of the active agent between the active agent reservoir and the fluid reservoir (e.g., preventing about 75% to about 100%, such as from about 95% to about 100%, of the initial amount of active agent from leaving the active agent reservoir and entering the fluid reservoir). In one embodiment, the volume of the active agent reservoir is smaller than the volume of the fluid reservoir (e.g., at least about five times larger or at least about ten times larger). In another embodiment, the fluid reservoir comprises additional semi-permeable membranes.

In another embodiment, the housing further comprises an inlet (e.g., a septum for receiving a needle) to allow fluid to enter the reservoir (e.g., the insertion of electrode medium into the fluid reservoir or the insertion of the active agent into the active agent reservoir). In another embodiment, the reservoir comprises the active agent (e.g., a lyophilized drug).

In another embodiment, the apparatus further comprises protrusions (e.g., needles or straight-tipped or curved-tipped blades) proximate to the delivery orifice where the protrusions are capable of piercing the stratum corneum of the mammal. In a further embodiment, the protrusions are capable of piercing the stratum corneum, but are not capable of substantially piercing the dermis.

In another aspect, the invention features a system for the delivery of an active agent through the body surface of a mammal comprising: a current supply unit; a first apparatus where the first apparatus comprises: (a) a first housing with a first delivery orifice, (b) a first reservoir within the first housing for containing the first active agent where the first reservoir is in communication with the first delivery orifice, (c) a first electrode within the first reservoir where the first electrode is in electronic communication with the current supply unit; and (d) a first sensor within the first reservoir where the first sensor is in electronic communication with the current supply unit; and a second electrode in electronic communication with the current supply unit; wherein the current supply unit can modify an electric parameter (e.g., electric parameters such as polarity, current intensity and current mode or waveforms) at the first electrode based upon feedback from the first sensor. The current supply unit provides the electric voltage/potential (e.g., it can reverse the polarity) as well as the electric current needed for the electrotransport (e.g., iontophoresis, electro-osmosis, and electroporation delivery) of the active agent from the reservoir, through the orifice, and into the mammal's body though the mammal's body surface. The current supply unit may connected to an external current source or comprise a battery.

In one embodiment, the system further comprises a second apparatus where the second apparatus comprises a second housing with a second delivery orifice and a second reservoir within the second housing containing the second electrode where the second reservoir is in communication with the second delivery orifice. In a further embodiment, the second apparatus further comprises a second sensor within the second reservoir where the second sensor is capable of being in electronic communication with the current supply unit and where the current supply unit can modify an electric parameter at the second electrode based upon feedback from the second sensor. In another embodiment, the system comprises three or more electrodes (e.g., between three and ten electrodes) in electronic communication with the current supply unit.

In another embodiment, the current supply unit may reverse the polarity at the first electrode. The length of the interval for each polarity reversal controlled by the current supply unit is based on the feedback signals (e.g., the pH or conductivity of the fluid in the fluid reservoir) relayed from the sensor(s). The relayed signals from the sensor(s) may also assist the current supply unit to modify the current mode and current intensity from the current supply unit to the electrodes in order to achieve the desired delivery rate.

In another aspect the invention features a method for delivering an active agent through a body surface of a mammal, the method comprising the steps of: affixing the orifice of the above mentioned apparatus to a body surface of the mammal (e.g., on the skin of a human); and connecting the electrode and the sensor to a current supply unit; wherein the current supply unit supplies current to the electrode and the current supply unit can modify an electric parameter at the electrode based upon feedback from the sensor.

In still another aspect, the invention features a method for delivering an active agent through a body surface of a mammal (e.g., the skin of a human), the method comprising the steps of: affixing the first orifice of the above mentioned system proximate to the body surface of the mammal; attaching the second electrode of the above mentioned system proximate to the body surface of the mammal (e.g., proximate to the first orifice) such that current passes from the first electrode to the second electrode through the body of the mammal; wherein the current supply unit supplies current to the electrode and the current supply unit can modify an electric parameter at the electrode based upon feedback from the sensor.

Other features and advantages of the present invention will be apparent from the detailed description of the invention and from the claims.

DETAILED DESCRIPTION OF THE INVENTION

Figure 1:
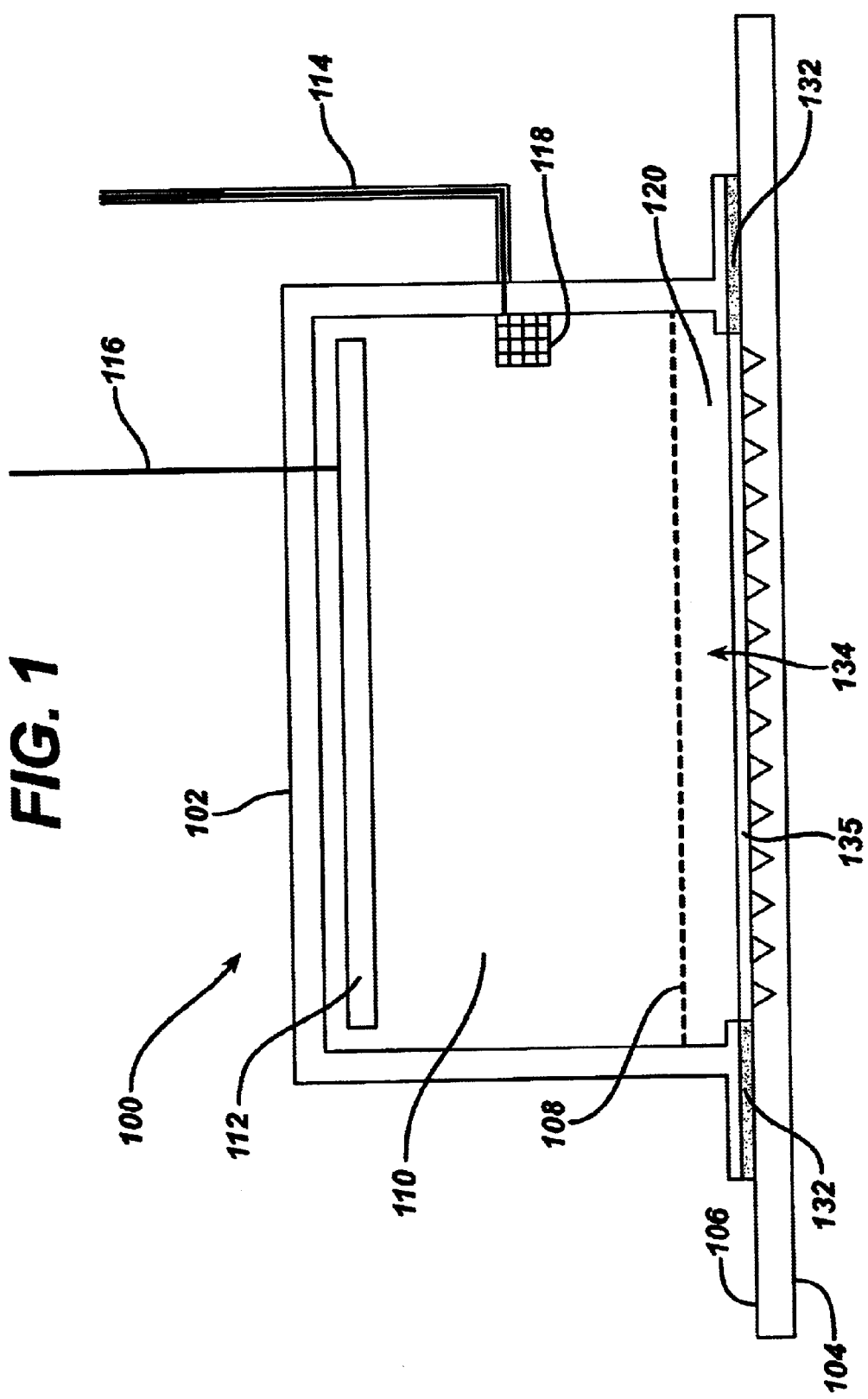
FIG. 1 is a schematic diagram of an embodiment of an apparatus according to the present invention.

It is believed that one skilled in the art can, based upon the description herein, utilize the present invention to its fullest extent. The following specific embodiments are to be construed as merely illustrative, and not limitive of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

The present invention relates to an improved electrotransport delivery system comprising a sensor within the delivery apparatus of the system. The advantage of the present invention is that the delivery system, because of the internal feedback sensors, operates under optimal condition since the system is able to make adjustments to compensate for compositional and electrical changes in the fluid of the system (e.g., drug content and non-drug ions). During an electrotransport delivery process, the active agents in the fluid reservoir immediately adjacent to the body surface are driven through the body surface by the electric repulsive force from the applied electric potential at the electrode. During this process, the sensors within the system detect certain composition changes within the fluid reservoirs, and communicate this information as electric signals to a current supply unit, which in one embodiment reverses the electric polarity of the conductive electrode to minimize competing ions and/or modifies the current intensity to achieve the desired delivery rate. In other embodiments, the relayed signals from the sensors may also assist the current supply unit to modify the current mode and intensity to achieve the desired delivery rate.

The additional improvement of adding the semi-permeable membrane within the reservoir reduces the competing ion concentrations in the drug reservoir, thereby enabling the direct use of injectable pharmaceutical products, which typically contain electrolytes such as buffers, antioxidants, chelating agents, preservatives, and salts for tonicity adjustment. During electrotransport drug delivery, these non-drug electrolytes act as competing ions, resulting in greater competition for transport of drug ions and hence lower the electrotransport drug delivery. See, e.g., Roberts, et al., "Solute Structure as a Determinant of Iontophoretic Transport", *Mechanisms of Transdermal Drug Delivery*, Potts, et al. Ed. Marcel Dekker, 1997, pages 329–331.

The waveforms of electric potential applied to the body surface and the electric current for electrotransport delivery, according the present invention include, but are not limited to, conventional direct current (DC), superimposed signals such as combining DC with conventional alternating current (AC) and that disclosed in U.S. Pat. No. 5,135,478, pulsed DC such as that disclosed in U.S. Pat. No. 5,042,975, and DC and pulsed DC with periodically reversed polarity as those described by Sun, et al. (*Proceed. Intern. Symp. Control. Rel. Bioact. Mater.*, 17:202–203, 1990, and U.S. Pat. Nos. 5,224,927 and 5,013,293. The electric current or potential waveforms may be tapered at any changing points (i.e., to avoid the abrupt and drastic current/potential changes) in order to reduce the associated discomfort and undesirable skin sensation. In one embodiment, the waveform of the electric current in the present invention is DC, or pulsed DC, with periodically reversed polarity. In one embodiment, the current density (e.g., current intensity per unit are of skin) is maintained by the sensors at less than about 0.5 mA/cm$^2$ (e.g., less than about 0.4 mA/cm$^2$).

As used herein, the term "active agents" refers drugs for treating diseases locally or systemically, nutrients or other biologically active compounds or herbal extracts, and minerals to improve general health or local skin/mucous tissue conditions. Active agents which may be delivered with this apparatus include, but are not limited to, any material capable of exerting a biological effect on a human body, such as therapeutic drugs, including, but not limited to, organic and macromolecular compounds such as polypeptides, proteins, and nucleic acid materials comprising DNA; and nutrients. Examples of polypeptide and protein active agents include thyrotropin-releasing hormone (TRH), vasopressin, gonadotropin-releasing hormone (GnRH or LHRH), melanotropin-stimulating hormone (MSH), calcitonin, growth hormone releasing factor (GRF), insulin, erythropoietin (EPO), interferon alpha, interferon beta, oxytocin, captopril, bradykinin, atriopeptin, cholecystokinin, endorphins, nerve growth factor, melanocyte inhibitor-I, gastrin antagonist, somatotatin, encephalins, cyclosporin and its derivatives (e.g., biologically active fragments or analogs). Other active agents include anesthetics; analgesics (e.g., fentanyl and salts thereof such fentanyl citrate); drugs for treating psychiatric disorders, epilepsies, and migraine; drugs for stopping drug additions and abuses; anti-inflammatory agents; drugs to treat hypertension, cardiovascular diseases, gastric acidity and ulcers; drugs for hormone replacement therapies and contrceptives; antibiotics and other antimicrobial agents; antineoplastic agents, immunosuppressive agents and immunostimulants; and drugs acting on blood and the blood forming argans including hematopoietic agents and anticoagulants, thrombolytics, and anti-platelet drugs. Other active agents that can be delivered into the body using the shear device in the present invention include vaccines for various diseases, such as those for influenza, AIDS, hepatitis, measles, mumps, rubella, rabies, rubella, avercella, tetanus, hypogammaglobulinemia, Rh disease, diphtheria, botulism, snakebite, back widow bite and other insect bite/sting, idiopathic thrombocytopenic purpura (ITP), chronic lymphocytic leukemia, cytomegalovirus (CMV) infection, acute renal rejection, oral polio, tuberculosis, pertussis, Haemophilus b, Pneumococcus, and *Staphylococcus aureus*. See, e.g., R. Ulrich, et al in Vaccine, Vol. 16, No. 19, pages 1857–1864, 1998. An example of a vaccine against staphylococcus intoxication is described in PCT Patent Application WO 00/02523. Also, other cationic and anionic active agents, such as those described in M. Roberts, et al., "Solute Structure as a Determinant of Iontophoretic Transport", *Mechanisms of Transdermal Drug Delivery*, R. O. Potts and R. H. Guy, Ed., Marcel Dekker, pages 291–349, 1997, may be delivered with this apparatus, e.g., by iontophoresis or passive diffusion. Active agents that are non-ionized or with a net charge equal to zero may also be delivered with this apparatus by electro-osmosis or passive diffusion.

Referring to FIG. 1, the apparatus 100 comprises a housing 102 having a removable release-liner 104 covering delivery orifice 134. The removable release-liner 104 will be removed prior to an electrotransport delivery exposing orifice 134, and the apparatus 100 will be affixed to the skin surface 106 with the adhesive layer 132. The housing 102 may be comprised of a silicone rubber, synthetic rubber, or natural rubber, such as poly(isoprene), poly(butadiene-co-styrene), poly(isobutene-co-isoprene), and poly (chloroprene); polyurethane; nylons; polystyrene; polycarbonate; and acrylic polymers. The housing 102 may be any shape (e.g., circular, oval, or rectangular) and size (e.g., dependent upon the volume of active agent to delivered and convenience if the device is to be worn by a patient). The contact surface of housing 102 to the skin surface 106 may be any shape (e.g., circular, oval, or rectangular) which an area of from about 1 to about 50 cm$^2$ (e.g., from about 5 to about 30 cm$^2$ or about 12 cm$^2$). The orifice 134 may be any shape (e.g., circular, oval, or rectangular). In one embodiment, the housing 102 comprises more than one orifice 134, e.g., various small holes within said housing in communication with the active agent reservoir 120 and the skin surface 106 (Not Shown).

The skin surface 106 (e.g., the human skin) may be intact in which case the active agents are iontophoretically delivered through the skin appendages (e.g., sweat glands and hair follicles) and intercellular spaces between keratinocytes of the stratum corneum. The body surface may also be damaged, such as in certain skin diseases (e.g., psoriatic skin lesions), wounds, and abrasions or perforations made by abrasive or sharp objects. The disruptions of the body surface may also be carried out purposely by attaching protrusions to the skin contacting surface of the device (e.g., proximate of adjacent to the orifice(s) of the device) in order to improve skin permeation of active agents (e.g., as disclosed in U.S. Pat. Nos. 3,964,482 and 5,250,023, PCT Patent Applications WO96/17648, WO97/48441, WO97/48442, WO 98/11937, WO 98/46124, and WO98/28037, and Henry, et al., J. Phann. Sci. Vol. 87, No. 8, pages 922–925 (1998).

In one embodiment, the housing comprises multiple orifices and multiple blades. The orifices and blades are formed from a single sheet of material (e.g., a thin sheet of metal such as stainless steel). The channels are formed by using a penetrator (e.g., a round or flat-sided awl) to pierce the sheet. As the penetrator pierces the sheet, the penetrator stretches the sheet until it pierces through the sheet, creating an orifice and tapered, tipped blades (e.g., the width of the resulting blades are wider at the bottom of the blade than at the top or tip of the blade, and the thickness of the edge of the blade is greater at the bottom than at the top of the blade). The blades, thus, surround the perimeter of the orifice. The number of blades created will depend on the shapes of the penetrator (e.g., a penetrator with four side will create four blades). The blades may also be curved towards the channel (e.g., if a conical or pyramidal penetrator is used). The manufacture of such orifices and blades are described in PCT Application No. WO98/11937.

Optionally, a semi-permeable membrane (Not Shown) may be present between the active agent reservoir 120 and the removable release-liner 104 or the skin surface 106 during use. Such a semi-permeable membrane allows the active agent to pass freely into the skin during iontophoresis, but retains any other ingredients (e.g., a suspending agent) in the active agent reservoir 120.

The electrode 112 may be made of a conductive material such as a noble metal such as platinum or gold, titanium, carbon, or made by plating the conductive material onto a substrate. Conductive polymers may also be used in the electrode 112. Suitable conductive polymers include, but are not limited to, conductive filler-embedded polymers, such as carbon-embedded silicone rubbers, carbon-embedded natural rubbers, and silver halide powder-embedded polymers. Various carbon-based electrodes may be constructed from glassy carbon, reticulated vitreous carbon, graphite/epoxy composites, pyrolytic graphite, carbon pastes, carbon powders, and carbon fibers. Other materials that may be used as the electrode 112 include, but are not limited to, silver halide-coated silver (e.g., AgCl-Ag, AgBr-Ag, AgI-Ag), corrosive resistant alloys (e.g., stainless steels and Ti-containing alloys). The electrode 112 may also be made with a combination of any of the foregoing materials. To utilize electrolysis of water, the conductive electrodes should be electrochemically inert, e.g., a platinum electrode.

The adhesive layer 132 affixes the apparatus to the body surface during electrotransport delivery. The adhesive in the adhesive layer may be a polymeric, pressure sensitive and/or nonconductive and remain adherent even after prolonged exposure to water. Typically, the adhesive has a broad working temperature range. Suitable adhesive materials include, but are not limited to, silicones, polyisobutylenes and derivatives thereof, acrylics, natural rubbers, and combinations thereof. Suitable silicone adhesives include, but are not limited to, Dow Corning® 355 (available from Dow Corning of Midland, Mich.); Dow Corning® X7-2920; Dow Corning® X7-2960; GE 6574 (available from General Electric Company of Waterford, N.Y.); and silicone pressure sensitive adhesives, such as those disclosed in U.S. Pat. Nos. 2,857,356, 4,039,707, 4,655,767, 4,898,920, 4,925,671, 5,147,916, 5,162,410, and 5,232,702. Suitable acrylic adhesives include, but are not limited to, vinyl acetate-acrylate multipolymers, including, such as Gelv® 7371 (available from Monsanto Company of St. Louis, Mo.); Gelva® 7881; Gelva® 2943; I-780 medical grade adhesive (available from Avery Dennison of Painesville, Ohio); and acrylic pressure sensitive adhesives, such as those disclosed in U.S. Pat. Nos. 4,994,267, 5,186,938, 5,573,778, 5,252,334, and 5,780,050.

A removable release-liner 104 is adhered to the adhesive layer 132 during storage. The selection of the removable release-liner 104 is dependent on the type of the adhesive in use, and is well known to a person skilled in the art. The release-liner 104 is typically a polymer sheet or a paper coated with a polymer, which has rather weak adhesion toward the adhesive layer 132, therefore allowing itself to be easily removed prior to electrotransport delivery without damaging the adhesive layer 132. In addition to, or in lieu of, the adhesive 132, the apparatus 100 may be fastened to the body surface with an elastic band, a band with a buckle (similar to a leather watch band), or a Velcro® band or the like (Not Shown).

Fluid reservoir 110, serving as the electrode chamber to house the electrode 112, is in communication with the electrode 12, the sensor 18, and active agent reservoir 120 (through a semi-permeable membrane 108). Cable 116 establishes electronic communication between the electrode 112 and the current supply unit (Not Shown). Similarly, cable 114 establishes the communication between the sensor 118 and the current supply unit.

The fluid reservoir 110 may contain a suspending material for holding the fluid (e.g., the electrode medium). Suitable suspending materials include hydrophilic, highly absorbent, porous materials. Examples of suitable porous materials include, but are not limited to, cotton-based gauze; nonwoven pad made of rayon or a mixture of rayon, polyester and/or other polymer fibers; foam and sponge-like materials comprised of polyurethane, polyester and/or other polymers; and cross-linked and non-cross-linked gelling materials, such as polyacrylamide, polyvinyl alcohol, gelatin, hydroxymethylcellulose, hydroxyethylcellulose, hydroxypropylcellulose, methylcellulose, and carboxymethylcellulose. In order to minimize ions in the electrode medium from competing with active agent ions for electric charge carrying across the body surface, electrode mediums should have low or no ionic charge. Generally, the electrode medium comprises an aqueous solution containing less than 1% (e.g., less than 0.1% or less than 0.01% by weight of electrolyte). In one embodiment, the electrode medium is water. The electrode medium may also contain from about 0.1 to about 90% by weight of other nonionic solvents, including, but not limited to, glycerin, propylene glycol, hexylene glycol, polyethylene glycol, polypropylene glycol, and low carbon-chain alcohols (such as ethanol and isopropyl alcohol).

The active agent reservoir 120 contains active agents in a solution during electrotransport delivery and is separated with the semi-permeable membrane 108 from the fluid reservoir 110. The aforementioned suspending material to hold the fluid in the fluid reservoir 110 may also be present in the active agent reservoir 120. Generally, the semi-permeable membrane 108 is permeable to solvents and low molecular weight excipients, such as low molecular weight buffer species and tonicity adjusting ions, but not permeable to the active agent to be delivered. In one embodiment, only particles which have less than half (e.g., less than about a quarter) of the molecular weight of the active agent are able to permeate through the semi-permeable membrane 108.

Many ionic active agents are known to participate in the electrochemical reactions at the surface of the electrode 112. The electrochemical reaction of the active agent often results in the degradation of the active agent or deposition of the active agent on the surface of the electrode 112, thus reducing or eliminating the therapeutic effect of the active agent. The semi-permeable membrane 108 inhibits the active agent from contacting the surface of the electrode 112, thereby preventing degradation of the active agent or the loss of the active agent due to deposition of the active agent on the surface of the electrode 112.

The semi-permeable membrane 108 may be comprised of cellulose; cellulose derivatives, such as Spectra/Por® dialysis membranes available from Spectrum of Houston, Tex., regenerated cellulose, cellulose acetates, and cellulose nitrate; mixtures of cellulose with other polymeric materials, such as cellulose/polyesters and cellulose/propylene; polyethylene; polypropylene; Teflon®; polytetrafluoroethylene; polyvinylidene fluoride; nylon; polysulfone; polyethersulfone; cuprophan; polymethyl methacrylate; ethylene vinyl alcohol; polysulfone; and polyacrylonitrile.

Most protein and peptide drugs are administered by injection. The injectable drug preparations usually contain ionic excipients including preservatives such as cresol, chlorocresol, benzyl alcohol, methyl p-hydroxylbenzoate, propyl p-hydroxybenzoate, phenol, thimerosal, benzalkonium chloride, benzethonium chloride, and phenylmercuric nitrate; stabilizing agents; antioxidants such as ascorbic acid, ascorbic acid esters, butylhydroxy anisole, butylhydroxy toluene, cysteine, N-acetylcysteine, sodium bisulfite, sodium metabisulfite, sodium formaldehydesulfoxylate, acetone sodium bisulfite, tocopherols, and nordihydroguaiaretic acid; buffers; chelating agents such as ethylenediaminetetraacetic acid and its salts; buffers such as acetic acid, citric acid, phosphoric acid, glutamic acid, and salts thereof; and tonicity adjusting agents such as sodium chloride, sodium sulfate, dextrose and glycerin. These ionic excipients compete with the active agent ions for carrying the electric current. Because the competing ions (i.e., the ionic excipients), are usually smaller and weigh less than the active agent ions, they can carry a significant amount of the electric current. Consequently, much of the electric current is diverted to moving the ionic excipients instead of the active agent ions resulting in lower delivery efficiency of active agents.

By using the semi-permeable membrane 108, the electrotransport apparatus of the present invention can significantly reduce the competing ion concentration in the active agent reservoir 120, thus increasing electrotransport delivery of the active agent even when an injectable preparation in the market is used. The competing ions from the drug preparation in the active agent reservoir 120 can easily pass through the semi-permeable membrane 108 into the electrode medium containing no electrolyte or a very low concentration of electrolyte in the fluid reservoir 110. The active agent reservoir 120, thus, will have a much smaller number of competing ions. Consequently, a great fraction of the electrical current into the body surface is carried by the active agent ions instead of competing ions, resulting in greater delivery of the active agent.

In general, the lower the volume ratio between the active agent reservoir 120 and the fluid reservoir 110, the more of the competing ions are forced from the active agent reservoir 120 and into the fluid reservoir 110. Consequently, the active agent delivery efficiency increases as the volume ratio decreases. For example, at a volume ratio of 1:9 between the actrive agent reservoir and the fluid reservoir, the competing ion concentration in the active agent reservoir 120, after the competing ions permeate through the semi-permeable membrane 108 to reach equilibrium with the fluid reservoir 110, will be 1/10th the concentration in the same apparatus without the semi-permeable membrane 108 and the separate fluid reservoir 110 with such as a volume ratio. If the volume ratio is 1:49, the competing ion concentration in the active agent reservoir 120 will be reduced by 1/50th. Therefore, it is preferable to minimize the volume ratio of the active agent reservoir 120 to the fluid reservoir 110. In one embodiment, the volume ratio is less than about 1:1 (e.g., less than about 1:10, less than about 1:20, or less than about 1:50).

Figure 2:
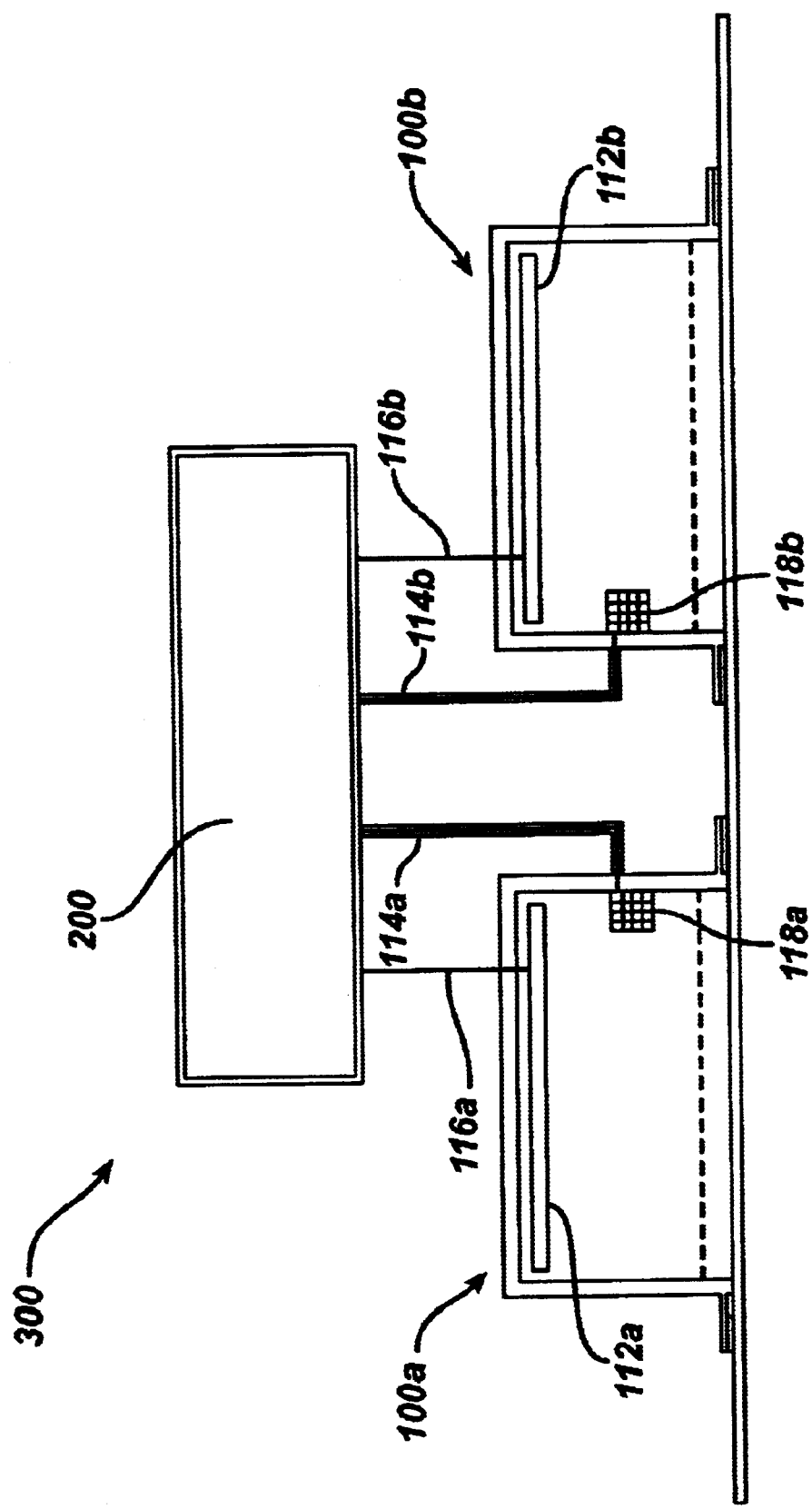
FIG. 2 is a schematic diagram of another embodiment of a drug delivery system comprising one pair of apparatuses according to the present invention.

In another embodiment shown in FIG. 2, the current supply unit 200 connects to one pair of the electrotransport apparatuses, 100a and 100b, to form a electrotransport delivery system 300. According to the present invention, the electric polarities applied from the current supply unit 200 to the electrodes 112a and 112b in apparatus 100a and apparatus 100b, respectively, may be reversed periodically by the current supply unit 200 based upon feedback from sensors 118a and 118b. Sensors 118a and 118b communicate with current supply unit 200 through cables 114a and 144b, respectively. The two active electrodes can simultaneously or sequentially deliver either the same active agent or different agents using simple direct current (DC) or pulsed DC. For example, insulin molecules carry positive charges in a solution at pH of 3, and carry negative charges at pH of 7. Simultaneous electrotransport delivery of insulin can be conducted at both electrodes when an insulin solution of pH of 3 is placed under the positive electrode, and another insulin solution of pH of 7 is placed under the negative electrode. When the electric polarity is reversed, iontophoretic insulin delivery ceases at both electrodes and restart after another polarity reversal. To deliver insulin in a sequential fashion, an insulin solution of the same pH value (e.g., pH of 7) may be placed under both electrodes, so that at a given time, only one electrode (i.e., the cathode) is delivering insulin. When the electric polarity is reversed, the other electrode will be delivering insulin until the next electric polarity reversal. Similarly, two different active agents, carrying either the same charge or the opposite charge in their respective solutions, may be delivered by the delivery system according to the present invention, by placing the solutions under the two electrodes and conducting iontophoresis with the aforementioned reversed polarity method.

The advantages of the reversed polarity method are described in details by Sun, et al., *Proceed. Intern. Symp. Control. Rel. Bioact. Mater.*, 17:202–203, (1990). Briefly, using pH control in a delivery system as an example, the reversed polarity reverses the directions of the electrochemical reactions concomitantly occurring at each electrode surface (i.e., the surface of the conductive material), hence neutralizing the hydrogen ions and hydroxyl ions generated at each electrode surface as a result of electrolysis of water, and preventing the undesirable pH shifting. For example, when noble metals are used as the conductive electrode material, hydrogen ions ($H^+$) are produced at the positive electrode (anode), and hydroxyl ions ($OH^-$) are generated at the negative electrode (cathode). The accumulation of access hydrogen ions at the anode during the first time interval shifts the pH of the electrode medium toward acidic (i.e., to a lower pH value), where as the accumulation of access hydroxyl ions at the cathode shifts the pH of the electrode medium toward alkaline (i.e., to a higher pH value). During the second time interval, however, the electrochemical reactions switched sides as the polarity is reversed: hydroxyl ions are generated at the electrode where hydrogen ions were generated during the first time interval, and vice versa for the other electrode. In this way each electrode medium returns to the original pH value at the end of the second time interval when the polarity change cycle is completed.

The iontophoresis technique of reversing polarity with a fixed frequency (i.e., with a constant time interval between each polarity reversal as described in the example above and in the prior art), however, works only in an ideal situation, and is a problematic under the real circumstances faced by drug delivery device products. There are many factors influencing a reverse-polarity iontophoresis process, which causes the solution pH to drift away from the initial pH value, and eventually diminishes iontophoretic delivery of the drug. For example, in addition to the water, other components of the composition in the electrotransport delivery system also participate the electrochemical reactions on the conductive electrode surfaces, which alter the amount of hydrogen ions or hydroxyl ions produced at each electrode, leading to the pH drifting. For example, chloride ions can be oxidized into chlorine gas at the anode. And antioxidants in the composition can also be oxidized. This problem is more serious when two different compositions are exposed to the electrodes such as when two active agents are delivered under each electrode, or when the electrochemical reactions occur in two different pH ranges. The impurities in the drug formulation and in the electrode components, as well as the difference in the fluid volumes between the two electrodes, will also leads to the drift from the original point or from an optimal electrotransport condition.

In one embodiment of the present invention resolves this problem by using a variable time interval for the polarity reversal based on the composition or electrical changes in the fluid detected by sensors. The electrotransport apparatus of the present invention is incorporated with one or more sensors. The sensors are in communication with the fluid, either the electrode medium in the fluid reservoir 110, as shown in FIG. 1, or the active agent solution in the active agent reservoir 120 (not shown).

As shown in FIG. 2 the sensors 118a and 118b detect the compositional or electrical changes resulting from current passage through the apparatus, and relay the signal to the current supply unit 200. Upon receiving the signal, the current supply unit 200 acts to reverse electric polarities on electrodes 112a and 112b in apparatus 100a and apparatus 100b, respectively. In this way, the current supply unit 200 dictates the length of the time interval between each reversal to assure the system is always operating under an optimal condition. The current supply unit 200 may also adjust the current intensity and current waveform to achieve the desired delivery rate. The examples of the composition changes in the fluid include but not limited to the changes in the solution pH, solution conductivity, the active agent(s), halide ions, anions of various acids and salts (e.g., sulfuric acid, nitric acid, phosphoric acid, acetic acid and citric acid), metal ions (e.g., sodium, potassium, lithium, strontium, calcium, zinc, magnesium and aluminum), compounds with amine functional groups, compounds with carboxylic acid functional groups, gases (e.g., oxygen, hydrogen, chlorine, carbon dioxide, ammonia), changes in color, viscosity, density, temperature and pressure, and the reactants and products of oxidation and reduction process on the conductive electrodes (e.g., metal and nonmetal species of various valences). The sensors may also detect the biological/chemical species from the mammal that enter the apparatus through its body surface, such as urea, lactic acid, creatinine, glucose, prostaglandins, electrolytes, amino acids, peptides and polypeptides, proteins and protein fragments, fatty acids and their esters, enzymes, hormones, and other metabolic products. The sensors of the present invention may be capable measuring any aforementioned changes in the contents of housing 102, and relay these information as signals to the current supply unit.

Thus, examples of sensors include, but are not limited to, conductivity and impedance sensors, ion-selective electrode sensors, sensors based on potentiometry such pH sensor and ion-selective electrodes (e.g., chloride, fluoride, sulfate, silver, sodium, potassium, lithium, and ammonium), sensors based amperometry or voltametry (e.g., oxygen and various amines), sensors based on colorimentry and spectrophotometry, pressure sensors, and temperature sensors. Examples of such sensors are disclosed in *Biosensors. Theory and Applications,* by D. G. Buerk, Lancaster, Pa., Technomic Publishing Company (1993), *Ion-Selective Micro-Electrodes. Principles, Design and Application,* by D. Ammann, New York, N.Y: Springer-Verlag (1986), in *Pharmaceutical Applications of membrane Sensors,* by V. V. Cosofret et al., Boca Raton, Fla.: CRC Press (1992), and in *Biosensor Principles and Applications,* L. J. Blum et al. Ed., New York, N.Y.: Marcel Dekker, Inc. (1991), as well as U.S. Pat. Nos. 5,591,124, 5,622,530, and 5,533,971 and PCT Patent Application WO98/146124. An example of a circuit for an electrotransport delivery device with an external sensor is disclosed in U.S. Pat. No. 5,213,568.

Optionally, certain buffering agents may be placed in the fluid reservoir 110 to maintain the pH of electrode medium within a given pH range during iontophoresis. Buffering agents include, but are not limited to, polymeric buffers, and solid materials which have a buffering effect to the surrounding liquid. Typically, these buffering agents can not pass through the semi-permeable membrane 108 to the active agent reservoir 120, because of the large molecular size of the polymeric buffer and the large particle size of the solid buffering materials (e.g., greater than about twice molecular weight cut-off of the semi-permeable membrane 108). The polymeric buffer may be any polymer that ionizes at a given pH by consuming hydrogen ions or hydroxyl ions and maintains the pH of the solution in the fluid reservoir 110. The solid buffering materials may be water insoluble or have only limited aqueous solubility. Suitable solid buffering materials include, but are not limited to, calcium carbonate and zinc oxide. The polymeric buffer may be water-soluble or water-insoluble. In one embodiment, the water-insoluble polymeric buffers are in the form of fine particles to maximize their surface area. Small particles of the polymeric buffer may be suspended in a gel matrix in which the active agent to be delivered is dissolved or suspended. Alternatively, the water insoluble polymeric buffer is formed into a porous or non-porous polymer membrane that covers the electrode 112 and/or the internal wall of the fluid reservoir 110. The porous polymer membrane may also be used as the semi-permeable membrane 108.

Polymers with acidic functional groups, e.g., anionic polymers such as the polymers used for enteric coating, may be used to prevent an increase in the pH of the electrode medium in the fluid reservoir 10 during cathodic iontophoresis (i.e., a negatively charged active agent delivered by a negative electrode). Suitable anionic polymers include, but are not limited to, copolymers of methacrylic acid and methacrylate, such as Eudragit L, S, RS and RL available from Rohm Tech, Inc. (Malden, Mass.); cellulose acetate phthalate; cellulose acetate trimellitate; and hydroxypropyl methylcellulose, such as C-A-P, C-A-T; and HPMCP 50 & 55 available from Eastman Fine Chemicals (Kingsport, Tenn.). In one embodiment, the anionic polymer is of a pharmaceutical grade.

One such anionic polymer is Eudragit S100. Below a pH of 7, Eudragit S100 is a solid. At a pH of 7 and above, Eudragit S100 dissolves due to ionization of its carboxyl groups. The ionization of the carboxylic acid functional groups leads to neutralization of the excess hydroxyl ions generated by the electrochemical reaction during cathodic iontophoresis. For example, a drug formulation that is intended to be administered by iontophoresis at a pH ranging from 6.5 to 7 may utilize Eudragit S100 as a buffering agent. At a pH of 6.5 to 7, Eudragit S100 is a solid and therefore does not interfere with the active agent delivery process. As the iontophoresis process at a cathode progresses, hydroxyl ions begin to build up in the solution of the fluid reservoir 110, which causes the Eudragit S100 polymer to dissolve and therefore the pH of the electrode medium is maintained.

Polymers with basic functional groups, i.e., cationic polymers, such as polymers with amine groups, may be used to prevent a decrease in pH during anodic iontophoresis (i.e., a positively charged active agent delivered by a positive electrode). Suitable cationic polymers include copolymers of dimethylaminoethyl methacrylate and methacrylic acid esters, such as Eudragit E available from Rohm Tech, Inc. In one embodiment, the cationic polymer is of a pharmaceutical grade. Eudragit E is solid above pH 5 and dissolves below pH 5. As the concentration of hydrogen ions increases due to the anodic electrochemical reaction, the Eudragit E is ionized by absorbing the hydrogen ions, thereby, maintaining the pH of the electrode medium.

The electrode medium in the fluid reservoir 110 may also contain other adjuvants, including, but not limited to, saccharides, polysaccharides, such as cyclodextrins, non-ionic surfactants, chelating agents, antioxidants, and antimicrobial agents.

Figure 3:
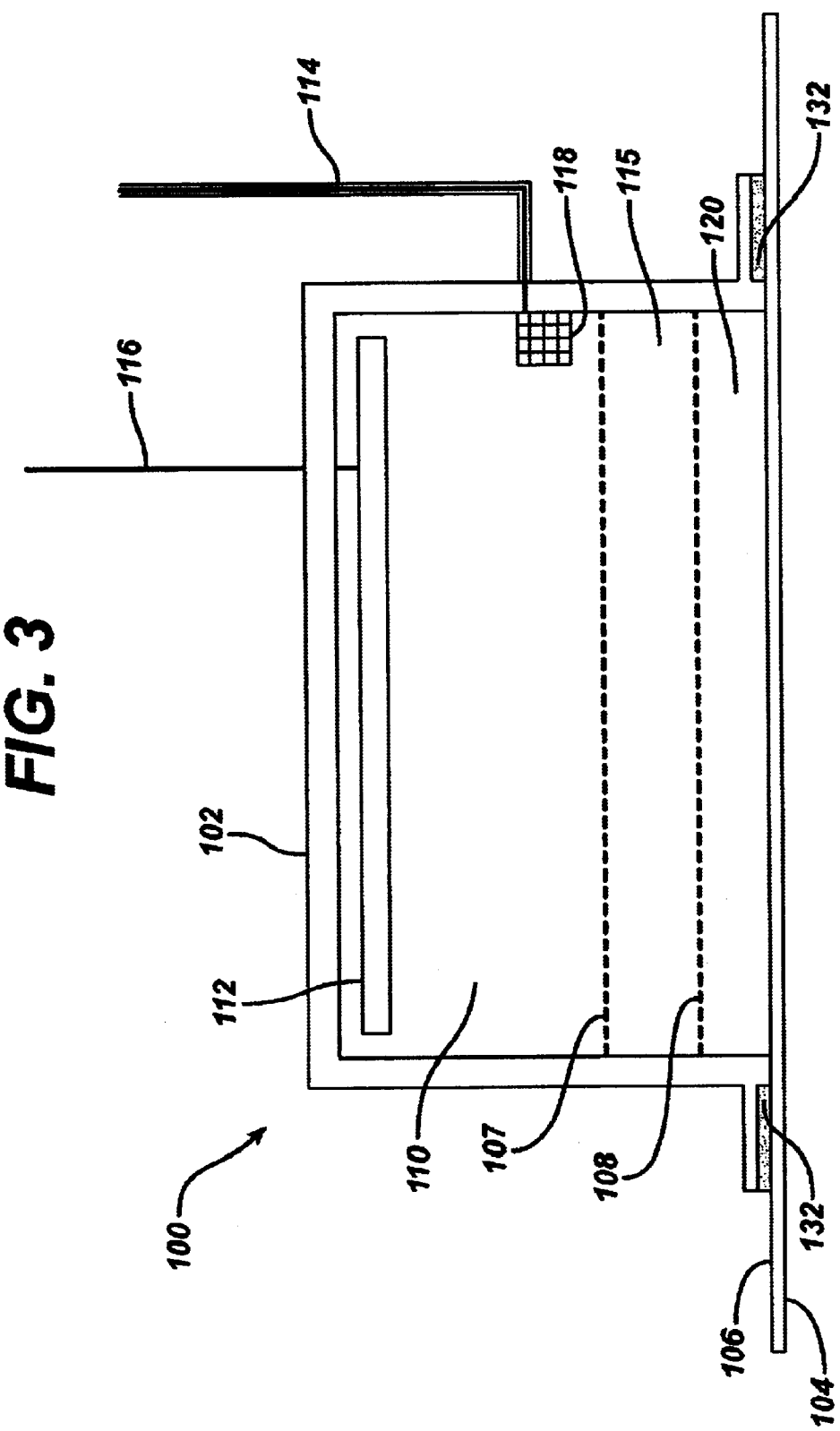
FIG. 3 is a schematic diagram of another embodiment of an apparatus including two fluid reservoirs and one active agent reservoir according to the present invention.

In yet another embodiment, the fluid reservoir 110 is split into two or more reservoirs which may be separated by another semi-permeable membrane(s) of different pore size (s) to allow only selected material to pass through. One such an example is shown in FIG. 3. The presence of the second semi-permeable membrane 107 creates another fluid reservoir 115, which is in communication with both the fluid reservoir 110 (through the second semi-permeable membrane 107) and the active agent reservoir 120 (through semi-permeable membrane 108). The fluid reservoir 115 may contain the aforementioned polymeric buffers and solid buffers, as well as ion-exchange resins, and optionally, the aforementioned suspending material. The fluid reservoir 115 may serve to remove the competing ions and to prevent them reaching active agent reservoir 120. Additional reservoirs may also included in the electrotransport apparatus to serve other purposes, for example, to remove the gases and other "wastes" generated from the electrochemical reactions on the conductive electrodes. The additional fluid reservoirs may be positioned between the top of the housing 102 (the side opposite the delivery orifice) and the conductive electrode 112.

The current supply unit 200 in FIG. 2 may be of any shape and size, and typically will be small if the system is intended to be worn by a patient. The current supply unit may receive its energy from an external source (e.g., the current supply unit is plugged into a standard wall outlet) or it may comprise a battery (e.g., if it is to be worn by a patient). In one embodiment, the current supply unit, the apparatus, and the second electrode are all contained within the same container. Examples of such systems and the circuits for such systems are well known in the art, e.g., U.S. Pat. Nos. 4,744,788, 4,747,819, 5,224,927, 4,752,285, 4,722,726, 4,731,049, 5,042,975 and 5,853,383. Examples of reverse polarity circuits are disclosed in U.S. Pat. Nos. 4,406,658 and 5,224,927.

Figure 4:
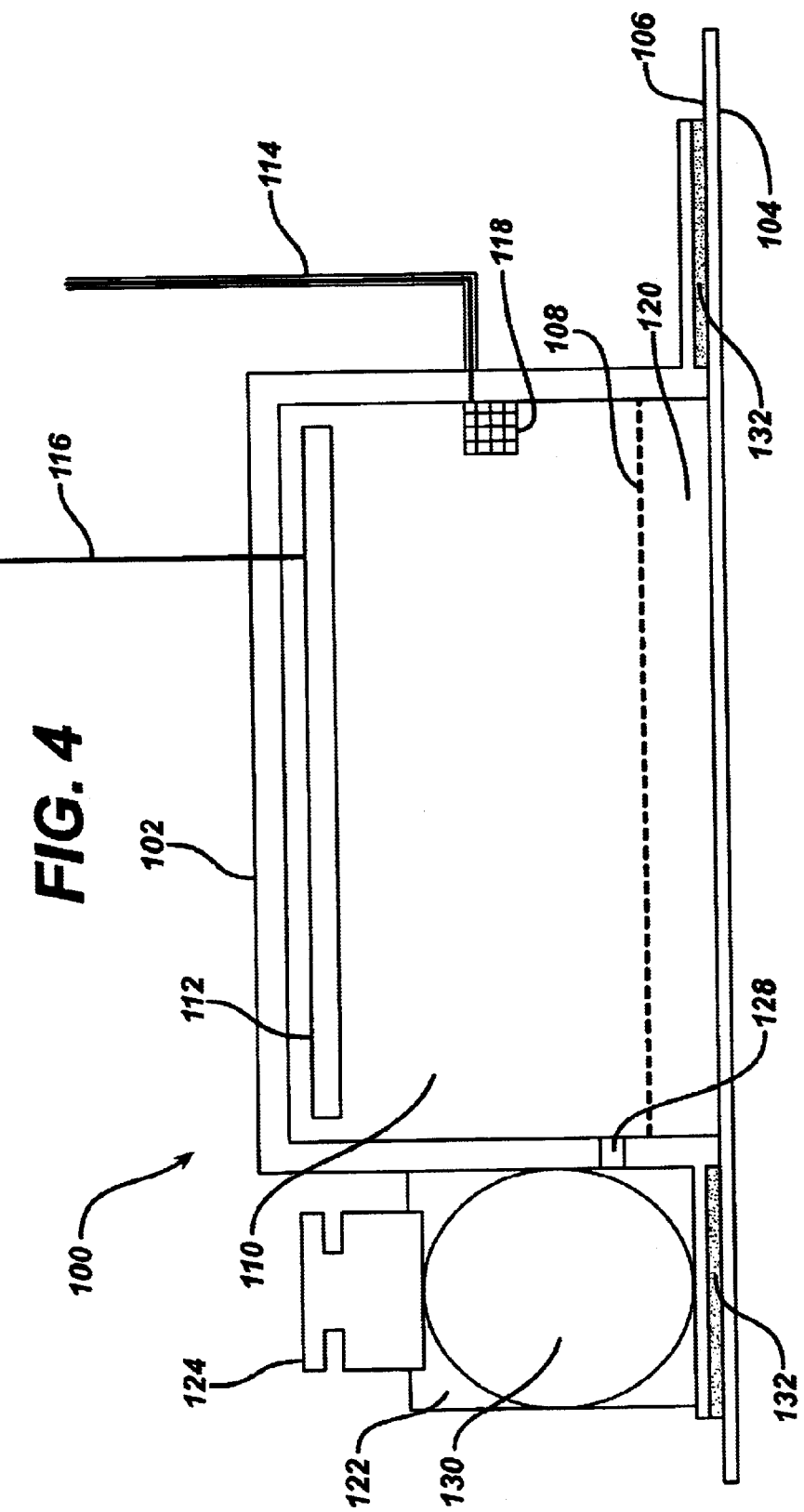
FIG. 4 is a schematic diagram of another embodiment of an apparatus including one storage capsule according to the present invention.

Referring to FIG. 4, an inlet 128 permits introduction fluids (e.g., the electrode medium) into the fluid reservoir 110 through an inlet 128. In one embodiment, the inlet 128 is adapted to receive electrode medium contained in capsule 130. Capsule 130 may be any shape (e.g., cylindrical or spherical). Capsule 130 may be made of any pharmaceutically acceptable material such as glass, plastic, or metal. For a glass capsule or other breakable capsule, a plunger 124 may be pressed against the capsule 130 in the chamber 122 to break the capsule 130 by crushing or piercing through the capsule wall. The solution in the capsule 130 then flows through the inlet 128 into the fluid reservoir 110.

The inlet 128 may optionally contain a filter to prevent broken pieces of the capsule 130, such as glass debris, from entering the fluid reservoir 110 and contacting the skin of the mammal.

The active agents with this embodiment may be preloaded in the active agent reservoir 120 either as powder immobilized in the aforementioned suspending material, for example, porous material (e.g., non-woven pad or polyurethane foam) or in a lyophilized form (i.e., by freeze-drying) with or without the porous material. In one embodiment, the solid-state drug is dissolved as the electrode medium enters the active agent reservoir 120 through the semi-permeable membrane 108 from the fluid reservoir 110. The pharmaceutical excipients necessary for drug stability during lyophilization process and storage, rapid dissolution, and solubilization may be present in the active agent reservoir 120. The examples of the excipients include, but are limited to, phosphoric acid, citric acid their pharmecutically acceptable salts, antioxidants, chelating agents, preservatives, human serum albumin, gelatin and carbohydrates such as dextrose, mannitol, dextran, and cyclodextrins.

Figure 5:
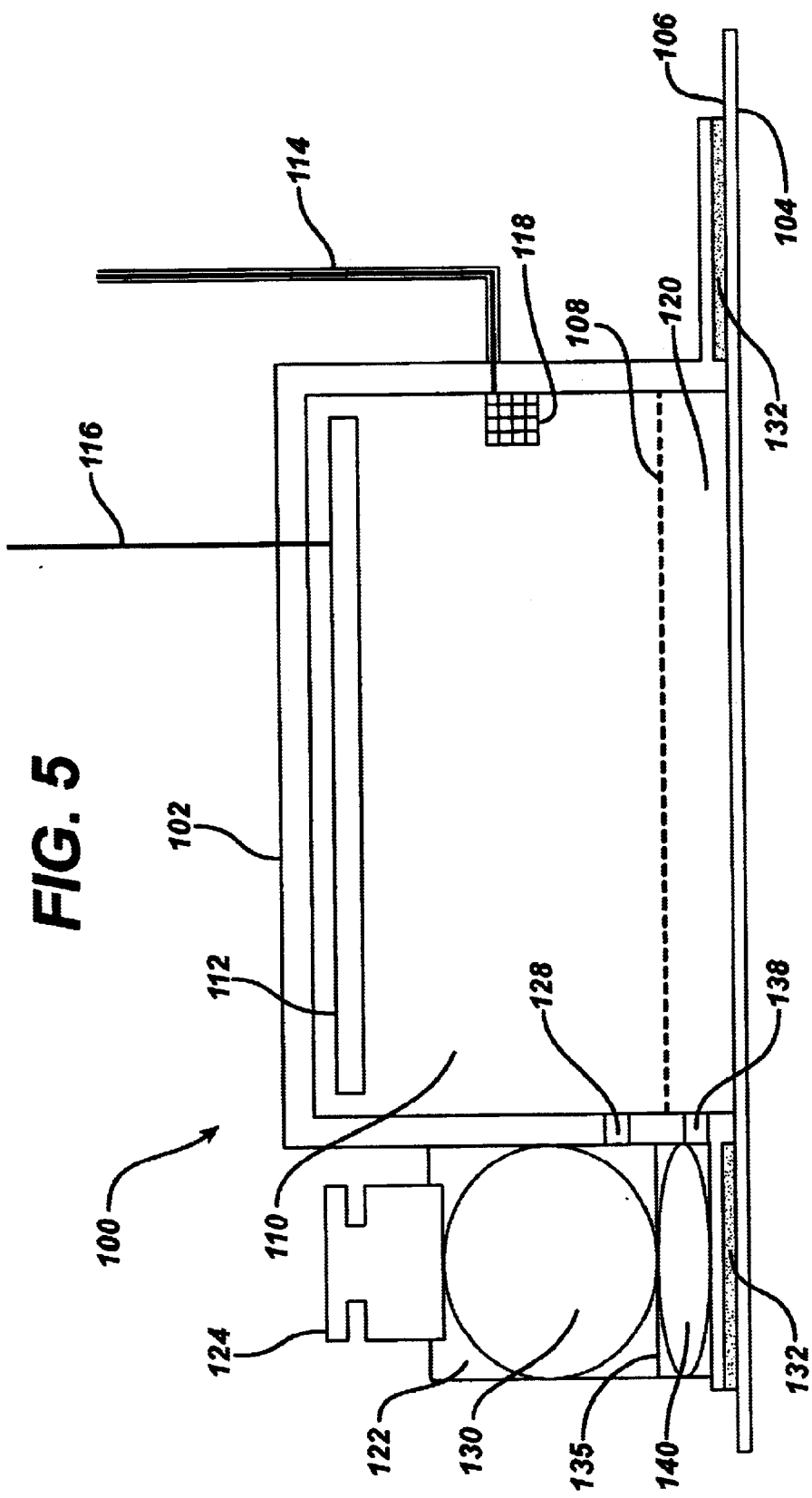
FIG. 5 is a schematic diagram of another embodiment of an apparatus including two storage capsules according to the present invention.

In another embodiment shown in FIG. 5, first capsule 130 and second capsule 140 are inserted into chamber 122. Second capsule 140 contains a solution containing the active agent. First capsule 130 contains a fluid, such as a low ionic or non-ionic liquid (e.g., distilled water) as the electrode medium. The partition membrane 135 separating the two capsules is impermeable to liquid, but is elastic enough (e.g., diaphragm-like) or movable (e.g., piston-like) to allow the force exerted by the plunger 124 to break both first capsule 130 and second capsule 140. To prepare the apparatus for electrotransport delivery, the plunger is pressed into the chamber 122 to break the first capsule 130 and second capsule 140. The drug solution from second capsule 140 enters the active agent reservoir 120 from the inlet 138, and the electrode medium from first capsule 130 enters the fluid reservoir 110 through the inlet 128. As the non-drug ions from the active agent reservoir 120 enter the fluid reservoir 110 through the semi-permeable membrane 108, the competing ion concentration in the drug reservoir is significantly reduced for the reasons described above, and the efficiency of electrotransport delivery is significantly increased. The drug-containing solutions suitable for this electrotransport apparatus may be standard liquid preparations for parenteral administration. In order to stabilize the drug for sufficient commercial shelf life, various stabilizing agents, many ionic in nature, are formulated in the preparation, such as buffers, antioxidants, chelating agents, and preservatives. Electrolytes, such as sodium chloride, are often added to the injectable preparations to make them isotonic. The electrotransport apparatus of this embodiment enables the direct use of the injectable preparations with much enhanced delivery efficiency. In another embodiment, the electrode medium and/or active agent solution is injected into the fluid reservoir 110 and active agent reservoir 120, respectively, with a syringe through an inlet (e.g., a self-sealing inlet such as a septum). In another embodiment, there may be one or more small orifices (e.g., with a diameter smaller than 100 $\mu$m on the wall of housing 102), which serves as air outlet when filling the liquid reservoir. The small orifice may be sealed after the liquid reservoirs are filled. The small orifices may also be used to release the gasses generated during electrotransport (e.g., by using a valve).

In order to utilize the apparatuses of the present invention, the apparatus and a second electrode (e.g., a second apparatus of the present invention) needs to connected to a current supply unit to form an active agent delivery system,. The current supply unit is the source of current to the electrode in the apparatus. The current supply unit can also modify various electric parameters at the electrode (e.g., modify the intensity of the current or the polarity at the electrode) based upon feedback from the sensor.

Figure 6:
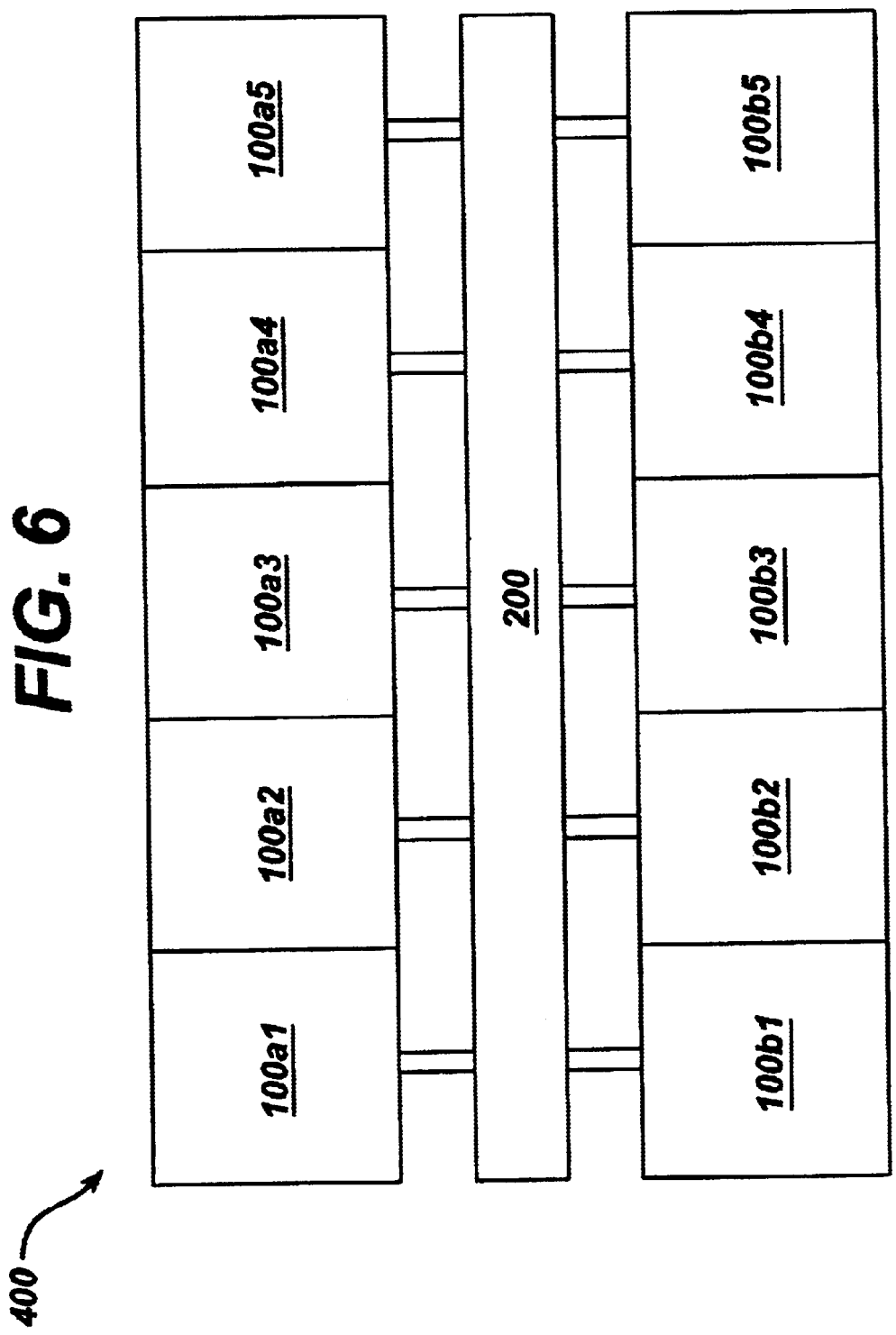
FIG. 6 is a schematic diagram of another embodiment of a drug delivery system comprising five pairs of apparatuses as an example of the multi-pair electrotransport delivery system according to the present invention.

In one embodiment, the system comprises a pair of aforementioned apparatuses during delivery operation as shown in FIG. 6. The current supply unit 200 is capable of operating each pair separately from the others, but is still capable of controlling the overall delivery of the whole drug delivery system. The arrangements and shapes of the combined pairs may vary, such as a square, circle, oval, rectangle, or triangle. One such an example in a rectangular configuration is shown in FIG. 6. Since several pairs of electrotransport apparatuses (e.g., 100a1 and 100b1) form a single electrotransport delivery system 400, the individual size of each apparatus's deliver orifice (i.e., the size of the apparatus's orifice) may be smaller than the orifice of a single-pair delivery system. For example, instead of using a simple paired delivery system with one active agent containing apparatus having an orifice covering 10 cm² of the skin, a 5-pair system as shown in FIG. 6 may provide the same skin coverage, i.e., 10 cm², under five apparatuses (i.e., 100a1 through 100a5). However, the orifice under each individual electrode (e.g., 100a1) in the five pair system only covers 2 cm² skin rather than 10 cm² of the skin in the single pair system. The advantages of a multi-pair system are improved control of electric current distribution, improved drug delivery, and reduced risk of the tissue injuries such as burn over the total delivery area. The resultant current distribution over the delivery area is more homogenous since the current supply unit can control each pair (e.g., a fraction of the total delivery area) separately, and can make necessary adjustment on applied electric potential in reference to its adjacent pairs. For example, if the skin area under a particular pair of apparatuses is damaged and the skin resistance drops or if the apparatus itself malfunctions due to damage or defect to one of its components, the current supply unit can, based on the signals from the sensors, modify the current intensity or polarity reversal interval, or even stop the electric current of this particular apparatus, to avoid any potential injury to the skin tissue. The current supply unit can also adjust the other apparatus(es) to compensate for the change caused by the failing apparatus thus improving the overall drug delivery.

Figure 7:
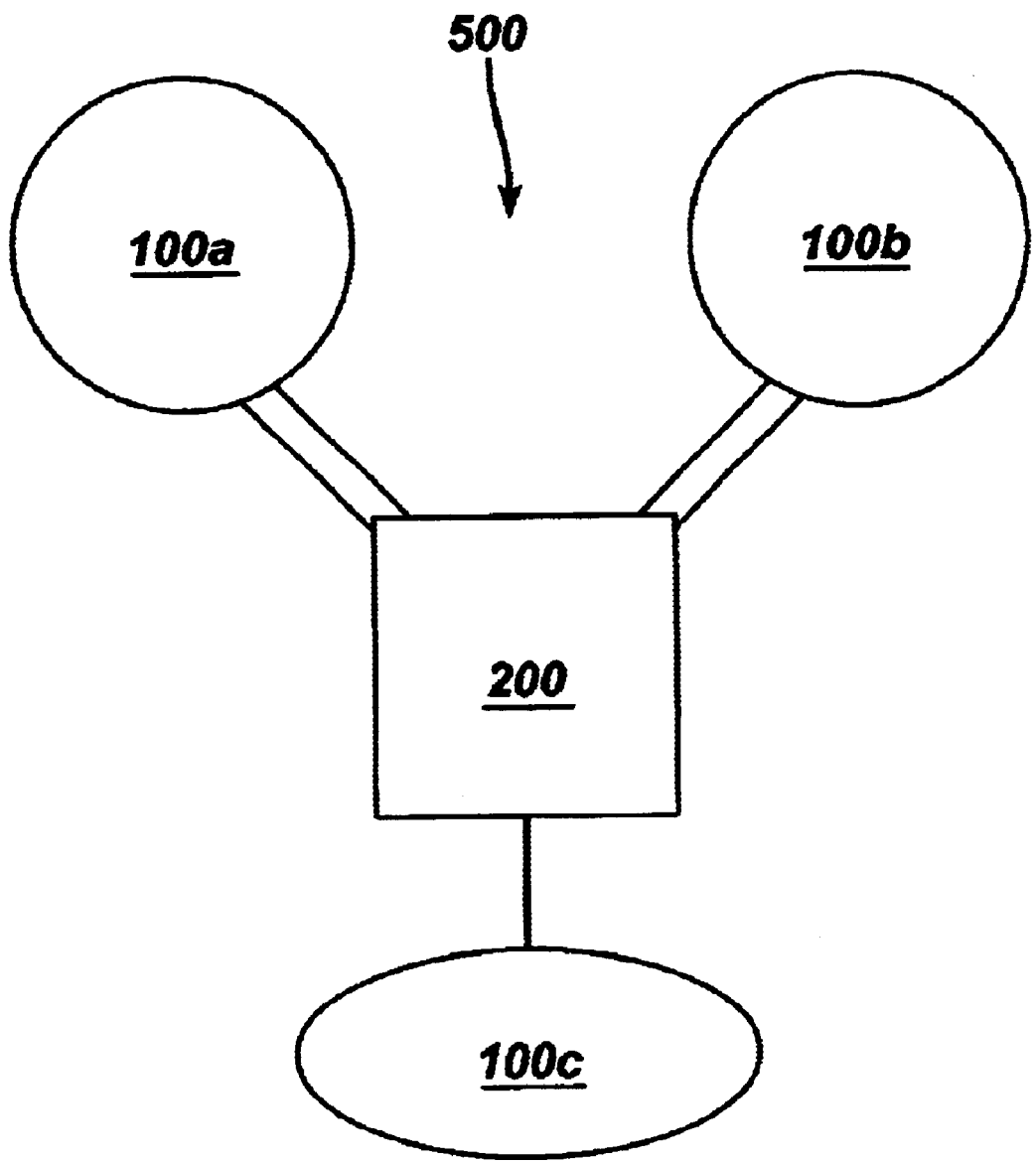
FIG. 7 is a schematic diagram of another embodiment of a drug delivery system comprising three apparatuses according to the present invention.

Referring to FIG. 7, another embodiment is a drug delivery system 500 comprises three aforementioned apparatuses (i.e., apparatuses 100a, 100b, and 100c). In one embodiment, while apparatuses 100a and 100b contain active agents, apparatus 100c contains no active agents and is filled with a buffer solution or buffer suspension, e.g., the fluid reservoir of 100c is filled with a buffer-containing liquid (e.g., the aforementioned polymeric buffer or solid buffer), while the active agent reservoir contains only electrolyte-containing liquid. An example of such an arrangement is disclosed in U.S. Pat. No. 5,540,669. The current supply unit 200 is in communication with the electrode of apparatuses 100a, 100b, and 100c and the sensors in apparatuses 100a and 100b. In another embodiment, the current supply unit 200 is also in electronic communication with the sensor of apparatus 100c.

There are various ways to conduct electrotransport drug delivery with the three-apparatus electrotransport delivery system 500. Two examples are described here to illustrate its operation modes. In the first operation mode, the electrotransport delivery is carried out in a manner similar to that depicted in FIG. 2 for the two-apparatus electrotransport system 300 (i.e., the electric polarity is reversed with the reversal interval determined by the current supply unit 200 based on the signals from the sensors in the apparatuses 100a and 100b). What makes system 500 in FIG. 7 different from system 300 in FIG. 2 is as follows. At a certain time point as detected by the sensors in the apparatuses 100a and 100b in FIG. 500, the iontophoresis operation between the electrotransport apparatuses 100a and 100b is temporally suspended. The third apparatus 100c is then electrically paired up with either the electrotransport apparatus 100a or 100b to adjust its ionic composition of the fluid in the reservoir of apparatus 100a or 100b to optimal electrotransport condition (e.g., a certain pH value) through the electrochemical reactions (e.g., electrolysis of water) on the respective electrode. Once the sensor indicates that the intended composition adjustment has been completed, the electrotransport drug delivery operated between the apparatuses 100a and 100b is resumed. Alternatively, apparatus 100c may be electrically paired up with either the electrotransport apparatus 100a or 100b to adjust its ionic composition by enhancing the electrochemical reactions in the apparatus involved (i.e., by simply increasing the current passage through that apparatus) without suspending the electrotransport delivery operation between the electrotransport apparatus.

In the second operation mode, both the electrotransport apparatuses 100a and 100b are simultaneously paired with the apparatus 100c that serves as a common counter electrode. The electrotransport delivery of the whole system is carried out by reversing the polarity periodically between the apparatuses 100a and 100c and between the apparatus 100b and 100c. The length of each reversal interval is determined by the sensors and current supply unit 200 to assure the drug compositions in the both 100a and 100b are always in the optimal range for electrotransport delivery. The presence of the buffer solution,. e.g., aforementioned polymeric buffers and/or solid buffers, maintains the composition in the apparatus 100c in a biologically compatible condition to avoid any undesirable side effects such as skin irritations. Any number of drug-containing apparatuses may be paired to apparatus 100c to operate in this mode of electrotransport (e.g., from one to ten apparatuses).

Similar to the system design of a multi-paired electrotransport delivery system 400 as shown in FIG. 6, multiple sets of three-apparatus units, each one of them represents the electrotransport delivery system 500 in FIG. 7, may be assembled together to form a multi-three-apparatus drug delivery system.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A system for the delivery of an active agent through the body surface of a mammal comprising:
   (i) a current supply unit;
   (ii) a first apparatus where said first apparatus comprises:
      (a) first housing with a first delivery orifice;
      (b) a first reservoir within said first housing for containing said first active agent where said first reservoir is in communication with said first delivery orifice;
      (c) a first electrode within said first reservoir where said first electrode is in electronic communication with said current supply unit; and
      (d) a first sensor within said first reservoir where said first sensor is in electronic communication with said current supply unit;
   (iii) a second apparatus where said second apparatus comprises:
      (a) a second housing with a second delivery orifice;
      (b) a second reservoir within said second housing for containing said second active agent where said second reservoir is in communication with said second delivery orifice;
      (c) a second electrode within said second reservoir where said second electrode is in electronic communication with said current supply unit; and
      (d) a second sensor within said second reservoir where said second sensor is in electronic communication with said current supply unit; and wherein said current supply unit reverses the polarity of said first electrode based upon feedback from said first sensor and reverses the polarity of the second electrode based upon feedback from said second sensor.

2. A system of claim 1, where said system comprises a third electrode in electronic communication with said current supply unit, where said third electrode is not in physical contact with the first reservoir or said second reservoir.

3. A method of claim 2, wherein said first active agent and said second active agent are the same active agent.

4. A method for delivering an active agent through a body surface of a mammal, said method comprising the steps of:
   (a) affixing said first orifice of said system of claim 2 to the body surface of said mammal;
   (b) affixing said second orifice of said system of claim 2 to the body surface of said mammal; and
   (c) affixing said third electrode of said system of claim 2 to the body surface of said mammal such that current passes from said third electrode to said first electrode and to the second electrode through the body of said mammal;
wherein said current supply unit supplies current to said first electrode and said second electrode, said current supply unit reverses the polarity of said first electrode based upon the feedback from said first sensor, and said current supply unit reverses the polarity of said second electrode based upon the feedback from said second sensor.

5. A method of claim 4, wherein said body surface is the skin of said mammal.

6. A method of claim 4, wherein said first active agent and said second active agent are the same active agent.

7. A system of claim 1, wherein said first sensor is selected from the group consisting of sensors for the measurement of pH, conductivity, impedance, said first active agent, ions, and biological compounds.

8. A system of claim 7, wherein said second sensor is selected from the group consisting of sensors for the measurement of pH, conductivity, impedance, said second active agent, ions, and biological compounds.

9. A system of claim 1, wherein said second sensor is selected from the group consisting of sensors for the measurement of pH, conductivity, impedance, said second active agent, ions, and biological compounds.

10. A system of claim 1, wherein said current supply unit modifies another electric parameter at said first electrode based upon feedback from said first sensor where said electric parameter is selected from the group consisting of current intensity and current waveforms.

11. A system of claim 10, wherein said current supply unit modifies another electric parameter at said second electrode based upon feedback from said second sensor where said electric parameter is selected from the group consisting of current intensity and current waveforms.

12. A system of claim 1, wherein said current supply unit modifies another electric parameter at said second electrode based upon feedback from said second sensor where said electric parameter is selected from the group consisting of current intensity and current waveforms.

13. A method of claim 1, wherein said first active agent and said second active agent are the same active agent.

14. A method for delivering an active agent through a body surface of a mammal, said method comprising the steps of:
   (a) affixing said first orifice of said system of claim 1 to the body surface of said mammal; and
   (b) affixing said second orifice of said system of claim 1 to the body surface of said mammal such that current passes from said first electrode to the second electrode through the body of said mammal;
wherein said current supply unit supplies current to said first electrode and said second electrode, said current supply unit reverses the polarity of said first electrode based upon the feedback from said first sensor, and said current supply unit reverses the polarity of said second electrode based upon the feedback from said second sensor.

15. A method of claim 14, wherein said body surface is the skin of said mammal.

16. A system of claim 14, wherein said first sensor is selected from the group consisting of sensors for the measurement of pH, conductivity, impedance, said first active agent, ions, and biological compounds.

17. A system of claim 16, wherein said second sensor is selected from the group consisting of sensors for the measurement of pH, conductivity, impedance, said second active agent, ions, and biological compounds.

18. A system of claim 14, wherein said second sensor is selected from the group consisting of sensors for the measurement of pH, conductivity, impedance, said second active agent, ions, and biological compounds.

19. A system of claim 14, wherein said current supply unit modifies another electric parameter at said first electrode based upon feedback from said first sensor where said electric parameter is selected from the group consisting of current intensity and current waveforms.

20. A system of claim 19, wherein said current supply unit modifies another electric parameter at said second electrode based upon feedback from said second sensor where said electric parameter is selected from the group consisting of current intensity and current waveforms.

21. A system of claim 14, wherein said current supply unit modifies another electric parameter at said second electrode based upon feedback from said second sensor where said electric parameter is selected from the group consisting of current intensity and current waveforms.

22. A method of claim 14, wherein said first active agent and said second active agent are the same active agent.

* * * * *